US006266435B1

(12) United States Patent
Wang

(10) Patent No.: US 6,266,435 B1
(45) Date of Patent: Jul. 24, 2001

(54) COMPUTER-AIDED DIAGNOSIS METHOD AND SYSTEM

(76) Inventor: Shih-Ping Wang, 409 Becker La., Los Altos, CA (US) 94022

( * ) Notice: Subject to any disclaimer, the term of this patent is extended or adjusted under 35 U.S.C. 154(b) by 0 days.

(21) Appl. No.: 09/179,205

(22) Filed: Oct. 27, 1998

Related U.S. Application Data

(63) Continuation-in-part of application No. 08/980,254, filed on Nov. 28, 1997, and a continuation-in-part of application No. 08/579,802, filed on Dec. 28, 1995, now Pat. No. 5,828,774, which is a continuation of application No. 08/129,255, filed on Sep. 29, 1993, now abandoned, said application No. 08/980,254, is a continuation-in-part of application No. 08/579,802, and a continuation-in-part of application No. 08/438,432, filed on May 10, 1995, now Pat. No. 5,729,620, which is a continuation-in-part of application No. 08/129, 255.

(51) Int. Cl.[7] ............................................. G06K 9/00
(52) U.S. Cl. ................................................ 382/132
(58) Field of Search ...................... 382/132, 133, 382/131, 130, 128; 378/28, 37; 128/922

(56) References Cited

U.S. PATENT DOCUMENTS 4,851,984 * 7/1989 Doi et al. ........................ 364/413.23
4,875,165 * 10/1989 Fencil et al. ........................... 364/413
4,908,876 * 3/1990 DeForest et al. ....................... 382/54
5,168,531 * 12/1992 Sigel ..................................... 382/48
5,321,681 * 6/1994 Ramsay et al. ........................ 369/69

* cited by examiner

Primary Examiner—Andrew W. Johns
Assistant Examiner—Seyed H. Azarian
(74) Attorney, Agent, or Firm—Cooper & Dunham LLP

(57) ABSTRACT

A computer-aided diagnostic (CAD) method and system provide image annotation information that can include an assessment of the probability, likelihood or predictive value of the CAD-detected suspected abnormalities as an additional aid to the radiologist. More specifically, probability values, in numerical form and/or analog form, are added to the locational markers of the CAD-detected suspected abnormalities. The task of a physician using a CAD system is believed to be made easier by displaying two different markers representing different probability thresholds. An additional threshold can be used to display "extra view markers" as an additional aid or guide to the radiologic technician to take extra views of a patient before the patient is released or discharged. A control device is added to allow the user to select and vary the probability threshold for the display of locational markers.

14 Claims, 3 Drawing Sheets

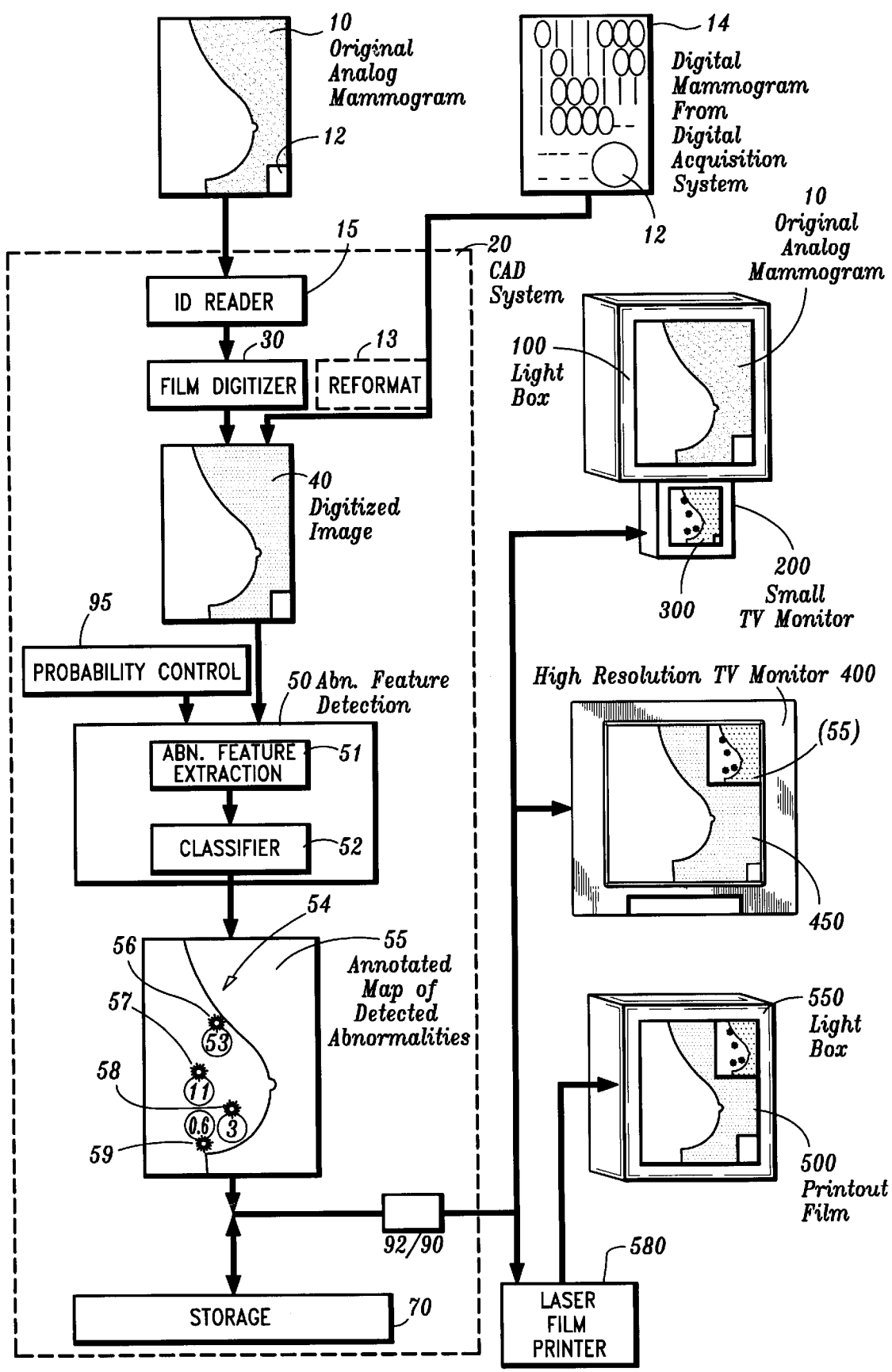

COMPUTER-AIDED DIAGNOSIS METHOD AND SYSTEM

REFERENCE TO RELATED APPLICATIONS

This application is a continuation-in-part of copending parent applications Ser. Nos. 08/980,254 filed on Nov. 28, 1997 and 08/579,802 filed on Dec. 28, 1995 (allowed and scheduled to issue as U.S. Pat. No. 5,828,774 on Oct. 27, 1998), which in turn is a continuation of parent application Ser. No. 08/129,255 filed on Sep. 29, 1993 (abandoned). Application Ser. No. 08/980,254 is in turn a continuation-in-part of said parent application Ser. No. 08/579,802 and of parent application Ser. No. 08/438,432 filed on May 10, 1995 (now U.S. Pat. No. 5,729,620), which in turn is a continuation-in-part of said application Ser. No. 08/129,255. This application hereby incorporates by reference the entire disclosure, drawings and claims of each of said parent applications as though fully set forth herein.

FIELD AND BACKGROUND

The method and system described in this patent specification relate to displaying radiological images and other information in a manner believed to assist their reading and interpretation by physicians or other users of the method and system. More specifically, the patent specification relates to a computer-aided diagnosis ("CAD") method and system for the detection and identification of anatomic abnormalities from radiological images viewed in conjunction with respective annotated road maps of the locations and/or characteristics of suspected abnormalities found through computer processing of the radiological images in accordance with the method and system described herein. The annotated maps highlight and/or identify characteristics of suspected abnormalities to help the user better assess the presence and/or meaning and significance of abnormalities in said radiological images.

The detection of suspected abnormal anatomic regions in radiological images using a computer system comprising specialized software and sometimes specialized hardware has been reported. For example, in the area of mammography, two books published in the last few years are: (1) "Digital Mammography," edited by A.G. Gale et al, published by Elsevier in 1994; and (2) "Digital Mammography '96," edited by K. Doi et al, published by Elsevier in 1996. This subject matter has also been discussed in recently issued patents, for example: U.S. Pat. Nos. 4,907,156 (Doi et al); 5,133,020 (Giger et al), 5,212,637 (Saxena); 5,331,550 (Stafford et al); 5,365,429 (Carman); 5,452,367 (Bick et al); 5,491,627 (Zhang et al), 5,537,485 (Nishikawa et al); 5,572,565 (Abdel-Moottaleb); (5,574,799 (Bankman et al); 5,579,360 (Abdel-Moottaleb); 5,586,160 (Mascio); 5,598,481 (Nishikawa et al); 5,615,243 (Gur et al); 5,627,907 (Gur et al); 5,633,948 (Kegelmeyer); 5,661,820 (Kegelmeyer); 5,657,362 (Giger et al); 5,666,434 (Nishikawa et al); 5,673,332 (Nishikawa et al); 5,729,620 (Wang); 5,732,697 (Zhang et al); 5,740,268 (Nishikawa et al); and 5,815,591 (Roehrig et al). Additionally, a commercial mammographic CAD system is being sold in this country under the trade name "ImageChecker" by R2 Technology, Inc., a licensee of applicant. See also, the parent applications identified above, including the references cited therein as prior art or otherwise. See also, copending patent application Serial No. 09/178,901, filed on Oct. 26, 1998 and entitled "Method and System for Computer-aided Lesion Detection Using Information from Multiple Images", now U.S. Pat. No. 6,075,879. The two books cited earlier, as well and the earlier-cited patent applications and patents, including the references cited therein, are hereby incorporated by reference in this patent specification as though fully set forth herein.

In a screening radiological procedure, such as screening mammography, the patients typically are asymptomatic and cancers are said to be found at a typical rate of about one to ten cases per one thousand patient examinations. Reading the mammograms, when the vast majority of them are negative, can be a tedious task. It has been reported that it is difficult for physicians to maintain a constantly high attention level.

Some abnormalities that can be detected or diagnosed from the mammograms can be missed or misdiagnosed, which can result in delayed or more costly treatment, and can even result in a reduction of a patient's longevity or chance of survival. According to an article in the May 26, 1993 issue of JAMA, pages 2616–2617, the misdiagnosis rate in mammograms can be in the range of 15 to 63%. Several mammography clinical studies, as summarized in an article entitled "Estimating the accuracy of screening mammography: a meta-analysis," published in Am. J. Prev. Med. (1998), volume 14, pages 143–152, indicate that the false negative (missed cancer) rate ranges from 5% to 17% for women's first screening and increases to 14% to 44% for subsequent screenings. The CAD system, serving as an electronic reminder or second reader, or as a spell-checker can be in a word processor, can assist physicians in attaining higher detection rate (higher sensitivity) for cancers or in reducing the misdiagnosis rate (lowering the false-negative rate).

Applicant understands that a current procedure using a commercial CAD system is as follows. The radiological technician or the physician takes a set of radiological images of the patient following a preprogrammed protocol or procedure. A physician views the radiological images and reaches a preliminary diagnostic decision. The physician next views separate, second images generated by said CAD method and system. Each second image is a copy or a sub-sampled (with fewer pixels) copy of a respective radiological image, marked or annotated with a localized notation of the suspected abnormalities the CAD system has detected through computer analysis of a digitized version of the respective radiological image. After any reexamination of the areas of the radiological images that correspond to the positions of the suspected abnormalities displayed on the CAD system, the physician makes a final diagnostic decision. The final diagnostic decision may or may not be the same as the preliminary decision, depending on whether the physician found the additional information provided by the CAD system to be significant and, if so, what significance the physician ascribed to it. Following the final diagnostic decision, and perhaps depending on the degree of suspicion for malignancy, the physician can recommend a course of further action, which can include no action for at least some period or time, or further follow-up examinations, or biopsy.

The following describes a typical procedure for detecting suspected abnormal anatomic features in mammograms using the commercial mammographic CAD system sold under the trade name ImageChecker. A set of four x-ray film mammograms, two views of each breast of a patient, taken by a radiological technician or a physician, are processed through a film digitizer to generate a set of four digitized images that are input as such into the ImageChecker system. Each of the four digitized images is then analyzed by a digital image processing computer with specialized software and typically some specialized hardware as well. The processing detects anatomic features that meet criteria for suspected abnormalities, and creates a respective annotated image for each of the film mammograms. The original film mammograms are then mounted on a conventional lightbox or a motorized lightbox, an alternator, for viewing. The annotated images of these mammograms are displayed on two small TV monitors located beneath the lightbox. Each small monitor displays two annotated images. Each annotated image comprises a sub-sampled digitized image of the respective film mammogram and locational markers marking the locations of the suspected abnormalities that the CAD processing detected. Currently, two different markers convey information regarding two key cancerous features of the suspected abnormalities that are detected. One marker is a triangle-shaped marker used to mark the location of a suspected abnormal cluster of microcalcifications. The other marker is a star-shaped marker used to mark the location of a suspected abnormal mass.

During a mammographic screening procedure, the CAD system typically over marks suspected abnormalities in order to ensure a high detection rate. Currently, the CAD systems in commercial use tend to report suspected abnormalities with relative probability values above a certain selected threshold, and at a rate much higher, perhaps a hundred times higher, than the rate at which a physician would judge the abnormality sufficiently suspicious to warrant a recall of the patient for additional diagnostic work-up examinations. Therefore, a physician may have to examine and perhaps dismiss not only the suspected abnormalities that a physician would detect from the film mammograms but also the typically greater number of suspected abnormalities detected by the CAD system. Depending on how many more additional suspected abnormalities the CAD system detects and identifies on the display, the extra task of dismissing them can slow down the reading and assessment process.

During a mammographic examination, the radiological technician sometimes takes extra views of a patient if the technician suspects or believes that an abnormality exists, or if a technical error is likely to have degraded a mammogram (such as patient motion, exposure error, positioning error, etc.). The added information from these extra views is believed to have the potential of enabling the physician to reduce recall rates by assisting in assessing/dismissing abnormalities. However, since some abnormalities are difficult to detect, sometimes even to a physician, there is little assurance that the technician can consistently detect and take extra views of these abnormalities.

SUMMARY

An object of the method and system described in this patent specification is to provide annotation information that can include an assessment of the probability, likelihood or predictive value of the CAD-detected suspected abnormalities as an additional aid to the radiologist or other user of the method and system. It is believed that an improvement in the display of the CAD information, by adding information such as probability information to the locational markers of the CAD-detected suspected abnormalities, would make it easier for the physician in assessing/dismissing the CAD-detected markers. A more specific object is to display a value in numerical form representing the probability, likelihood or predictive values of the CAD-detected suspected abnormalities, next to the locational markers of the CAD-detected suspected abnormalities. Another object is to use the locational markers of CAD-detected suspected abnormalities to display a value such as probability of the CAD-detected suspected abnormalities in analog form by varying the shape, size and/or the color of the locational markers. Still another object is to display only a few, e.g., two or three, different (in shape, color, etc.) locational markers for each type of the CAD-detected suspected abnormality (such as clusters of microcalcifications, mass, etc.), wherein each different marker represents a different threshold of information such as probability. Still another object is to provide a display of so-called "extra view markers" as an additional aid or guide to the radiologic technician so that extra views may be taken of the patient before the patient is released or discharged. It is believed that with the added information from these extra views, the physician can perform the examination with improved accuracy and that this can result in a reduced patient recall rate. Yet another object is to provide a control device to allow the user to select the threshold for information such as probability for the display of locational markers.

In a first exemplary and non-limiting embodiment of the method and system described in this patent specification, probability values in numerical form, representing the probability, likelihood and/or predictive values of the CAD-detected abnormalities, are displayed next to the locational markers of the CAD-detected suspected abnormalities on the annotation maps. In a second exemplary embodiment, the locational markers of CAD-detected suspected abnormalities display probability values of the CAD-detected suspected abnormalities in analog form by varying the shape, size or the color of these locational markers. In a third exemplary embodiment, two different locational markers representing two different selected probability thresholds are displayed on an annotated map of the CAD-detected abnormalities. In a fourth embodiment, so-called "extra view markers", representing a selected probability threshold, are displayed as an additional aid to the radiologic technician so that extra views may be taken of the patient before the patient is released or discharged. In a fifth exemplary embodiment, a control device is provided to allow the user to select and vary the probability thresholds for the display of locational markers.

Stated in broader terms, one aspect of the method and system described herein is to provide annotation information that can include an assessment of the probability, likelihood or predictive value of the CAD-detected abnormalities as an additional aid to radiologists, radiologic technicians, or other users.

BRIEF DESCRIPTION OF THE DRAWINGS

FIG. 1 is a schematic diagram, according to a first exemplary embodiment, illustrating a CAD system having a abnormality classifier to provide probability values of the CAD-detected suspected abnormalities and a display for displaying annotation maps with probability values in numerical form, representing the probability, likelihood or predictive values of CAD-detected suspected abnormalities, adjacent to locational markers of the CAD-detected suspected abnormalities as an additional aid to the user. FIG. 1 also illustrates a fifth embodiment wherein a control device is provided to allow the user to select and vary the probability threshold for the display of locational markers.

FIG. 3 also illustrates, according to a fourth embodiment, the selection and placement of "extra view markers" thresholds.

DETAILED DESCRIPTION

Figure 2A:
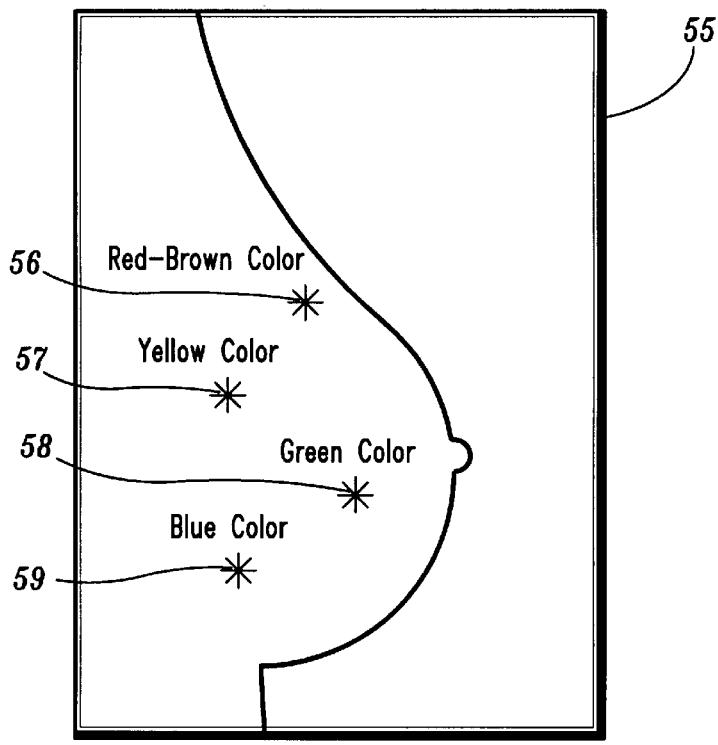
FIG. 2A illustrates an annotation map having colored locational markers, wherein the probability values are displayed in analog form in a spectrum of colors, according to a second embodiment.

Referring to FIG. 1, a preferred but non-limiting example of the method and system described herein involves providing annotation information that can include assessments of the probability, likelihood or predictive values of CAD-detected suspected abnormalities, in addition to the locational information, as an aid to the radiologist or other user of the method and system. In this example, the radiologic image is in the form of a mammographic x-ray film, which is acquired with a conventional mammographic film-screen imaging system. The original analog two-dimensional mammographic x-ray film 10 is sent through the film digitizer 30 of a CAD (computer-aided diagnosis) system 20 (such as that disclosed in said U.S. patents and applications incorporated by reference herein) to obtain a digitized two-dimensional mammographic image 40. Preferably, the film digitizer 30 is a high resolution CCD or laser film digitizer and has a dynamic range and a spatial resolution comparable to those of the original mammographic film that typically has a dynamic range of 3,000:1 to over 10,000:1 and spatial resolution of approximately 50 to 100 microns per pixel (or about 4,000×5000 to 2,000×2500 pixels for an 8 inch×10 inch film mammogram). The identity of the original mammographic image 10 also is preferably entered into the CAD system 20 at this point to identify the digitized mammographic image 40. A useful option at this point is to automatically input the identity of the original mammographic image 10 into the CAD system 20. This can be accomplished, for example, by first labeling the mammographic film 10 with a code such as a bar code, and then by reading the label into the CAD system 20 with an optional ID bar code reader 15 as the mammographic film 10 is being fed into the film digitizer 30.

The digitized mammographic image 40 is sent through an abnormal feature detection stage 50 of the CAD system 20. Key components of the abnormal feature detection stage 50, the abnormal feature extraction sub-stage 51 and the classifier sub-stage 52, have been described in detail in said U.S. patents and applications incorporated by reference herein. The output of the abnormal feature extraction sub-stage 51 is usually the features and locational information of the detected suspected abnormalities, The output of the classifier sub-stage 52 is usually the probability information of the detected abnormalities. Although several types of neural network classifiers (particularly feed-forward, multi layer, neural network classifiers) have been used in radiological CAD systems, other usable classifiers have been described, for example, in a book by K. Fukunaga (entitled: "Introduction to statistical pattern recognition", published by Academic Press in 1990) and a book by R. Duda and P. Hart (entitled: "Pattern Classification and scene analysis", published by John Wiley & Sons in 1973).

The findings or results from the abnormal feature detection stage 50 are in the form of a two-dimensional annotation map or x-y coordinate information 55 of the locations of the CAD-detected suspected abnormalities with probability values above a certain selected threshold. Four CAD-detected suspected abnormalities have been found (in this illustrative example) through the analysis of the digitized version 40 of the original film 10, and are illustrated at 56, 57, 58 and 59 at annotation map 55. For the purpose of illustration, let the abnormalities 56, 57, 58 and 59 have relative probability values of say 53, 11, 3 and 0.6 respectively. The display probability threshold is set in this example at 0.5; therefore, all four abnormalities, 56, 57, 58 and 59 are displayed. If the display probability threshold were set at 5, only abnormalities 56 and 57 would be displayed. Thus, the markers identify not only the detected location but also can have a relative probability value above a certain preselected threshold. The annotation map or x-y coordinates 55 can be scaled down to the size of a sub-sampled digital image of the respective film mammogram, say 512×512 pixel in size and 8-bit in gray scale version 41 of the digitized image 40, and the scaled-down image 41 and the annotation map 55 can be superimposed on each other in registration to form a miniaturized annotated road map image 300 that can be displayed and used as discussed below. The annotated map 55 can be shown with the breast outline 54, but the breast outline can be removed from the combined image 300 resulting from superimposing the map 55 and the reduced size breast image 41. One or more of the CAD-generated annotation map 55, the reduced size digital image 41, the combined image 300, and the digitized image 40 and its corresponding identification, can be stored for later use in an optional memory storage unit 70 in digital form. As also shown in FIG. 1, according to the first embodiment, the relative probability values are also displayed adjacent to the locational markers 56, 57, 58 and 59.

The annotation road map image 55 is transferred to an output display section of the system for display. The output display section of the CAD system can be a part of the total CAD system, in which case the data transfer can be conducted through a dedicated shielded cable. Or, the output display section can be a separate system, in which case an additional data storage memory may be added to the unit to store the transferred interim data and the data transfer may be conducted through a dedicated shielded cable or an existing network to where the viewing equipment is installed.

It is important to point out and emphasize the abnormal features of the CAD detected abnormalities to the physician, because it is believed that the physician, even after seeing the location of the CAD detected abnormalities on the miniature road map 55, can fail to notice or appreciate these abnormal features on the original x-ray film mammogram. By pointing these abnormal features out to the physician with further emphasis on the relative probability value, it is believed that the physician would be in better position to assess the meaning and significance of these CAD detected suspected abnormalities.

Also illustrated in FIG. 1 is a CAD output display comprising a conventional film illuminator 100, commonly called a lightbox, and a small TV monitor 200. Monitor 200 displays the combined annotated image 300 resulting from superimposing in registration the annotated road map 55 (preferably with the breast outline 54 removed) and the reduced scale digital image 41. By operating a toggle switch 90 the user can turn on-and-off the image 300 at TV monitor 200. If the user views the typical four film mammograms at the same time on lightbox 100, two monitors 200 can be used at the same time, each showing two respective annotation maps 55 or a single annotation map each that the user can select through an appropriate switch.

The dimensions of the display screen of the small TV monitor 200 in this example are of the order of ¼ to ½ of the dimensions of original x-ray film mammogram 10. Because a physician usually views a set of four mammograms from each patient at a time, two small TV monitors 200 can be used to display 2 or all 4 annotated road maps 55 of the corresponding film mammograms. During a physician's reading session, each small TV monitor 200 preferably is located or moved to (if mounted on a movable device such as an arm) as close as practical to the original film(s) 10 displayed at light box 100. Preferably the center of each small TV monitor 200 should be less than 12 inches from the center of the respective original film(s) 10 on the conventional film illumination light box 100 to minimize eye movement.

Again referring to FIG. 1, a preferred but non-limiting example, according to the first embodiment, can receive radiological images 14 that are already in a digital format, and detect suspected abnormalities on these radiological images with the CAD system 20 and print out these radiological images together with CAD results on photographic film. Digital imaging systems, such as magnetic resonance imaging ("MRI") systems, computed tomography ("CT") systems, ultrasound imaging systems, scintillation cameras, computed radiography ("CR") systems (such as Fuji's CR system based on stimulated emission phosphor detector), and recently reported flat panel type (using amorphous silicon array detectors) digital radiography and digital mammography systems, provide radiological images in the digital format. In this nonlimiting example, the radiological image is in the form of a digital mammogram 14, which is acquired with a digital mammography system. This digital mammogram 14, preferably already having a properly encoded identification and patient information 12, is reformatted at 13 into a digitized mammographic image 40 and is sent through the abnormal feature detection stage 50 of the CAD machine 20. If the digital image 14 is already properly formatted for the CAD machine 20, it is sent directly to and through the abnormal feature detection stage 50 of the CAD machine 20 without reformatting, as the initial film digitization step used in analog x-ray film example is not needed in this case.

There are several methods to display the CAD results and the digitally acquired mammogram. Because a digital system typically produces no film at the data acquisition stage, a first method is a totally filmless display by using a high resolution TV monitor 400. The resolution should be at least 1000×1000 pixels. In this method the annotation road map 55 (or a combined image corresponding to image 300) and the digital mammogram 40 are all displayed on the same TV monitor 400 as a combined digital image 450 as shown in FIG. 1. The annotation road map image 55, with the relative probability values displayed adjacent to the locational markers 56, 57, 58 and 59, can be displayed on top of and in registration with the digital mammogram 40, or it can be displayed at a margin or edge of the digital mammogram 40 (as illustrated). By operating a toggle switch 90 the user can turn on-and-off the annotation road map 55 from the image 450. A second display mode of the digitally acquired mammogram is to print out the digitized mammogram 40 on a photographic film 500 and view it at a lightbox 550. The annotation road map 55 (or a combined image corresponding to image 300), with the relative probability values displayed adjacent to the locational markers 56, 57, 58 and 59, can be placed on the same edge or margin of the printout film as the patient information label 12. The photographic film printout, typically having a resolution of 4000×5000 pixels, can be made with a high resolution laser film printer 580. Such high resolution, 4000×5000 pixels, laser film printers are commercially available with a resolution of 40 microns per pixel for 8 inch×10 inch size films and 100 microns per pixel for 14 inch×17 inch size films. It is sometimes preferred that only the miniaturized annotation road map 54 of the annotation map image 55 be printed on the edge of the printout film 500 or over the entire film.

FIG. 2A, according to a second embodiment, illustrates the annotation map 55 having colored locational markers 56, 57, 58 and 59. For example, "false" colors are assigned to represent the relative probability values in much the same way as "false" colors are assigned to represent elevation in a topographical map.

Figure 2B:
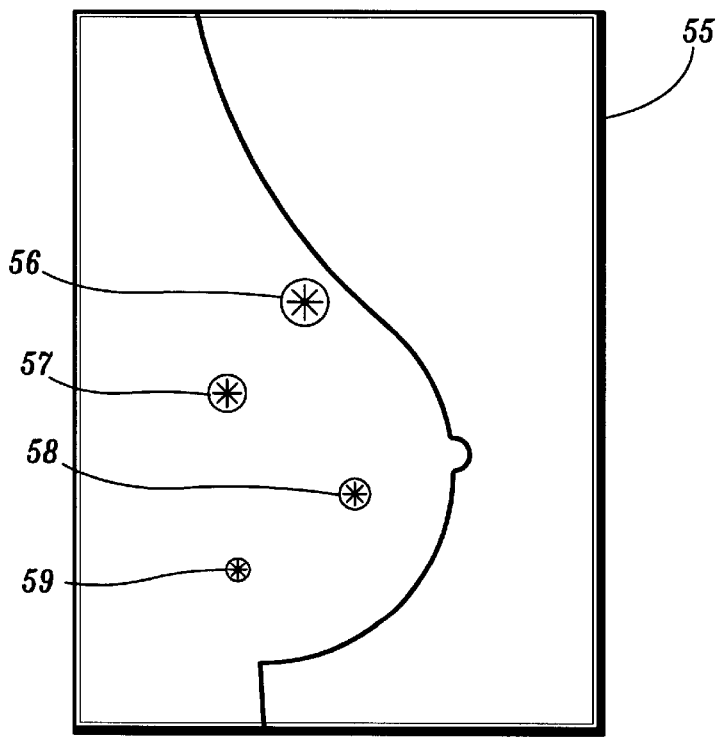
FIG. 2B illustrates an annotation map having differently sized locational markers, wherein the probability values are displayed in analog form according to the size of the locational markers, according to an alternate second embodiment.

FIG. 2B illustrates the annotation map 55 having differently sized locational markers 56, 57, 58 and 59, whereas the relative probability value is displayed in analog form, represented by the size of the locational markers.

Figure 3:
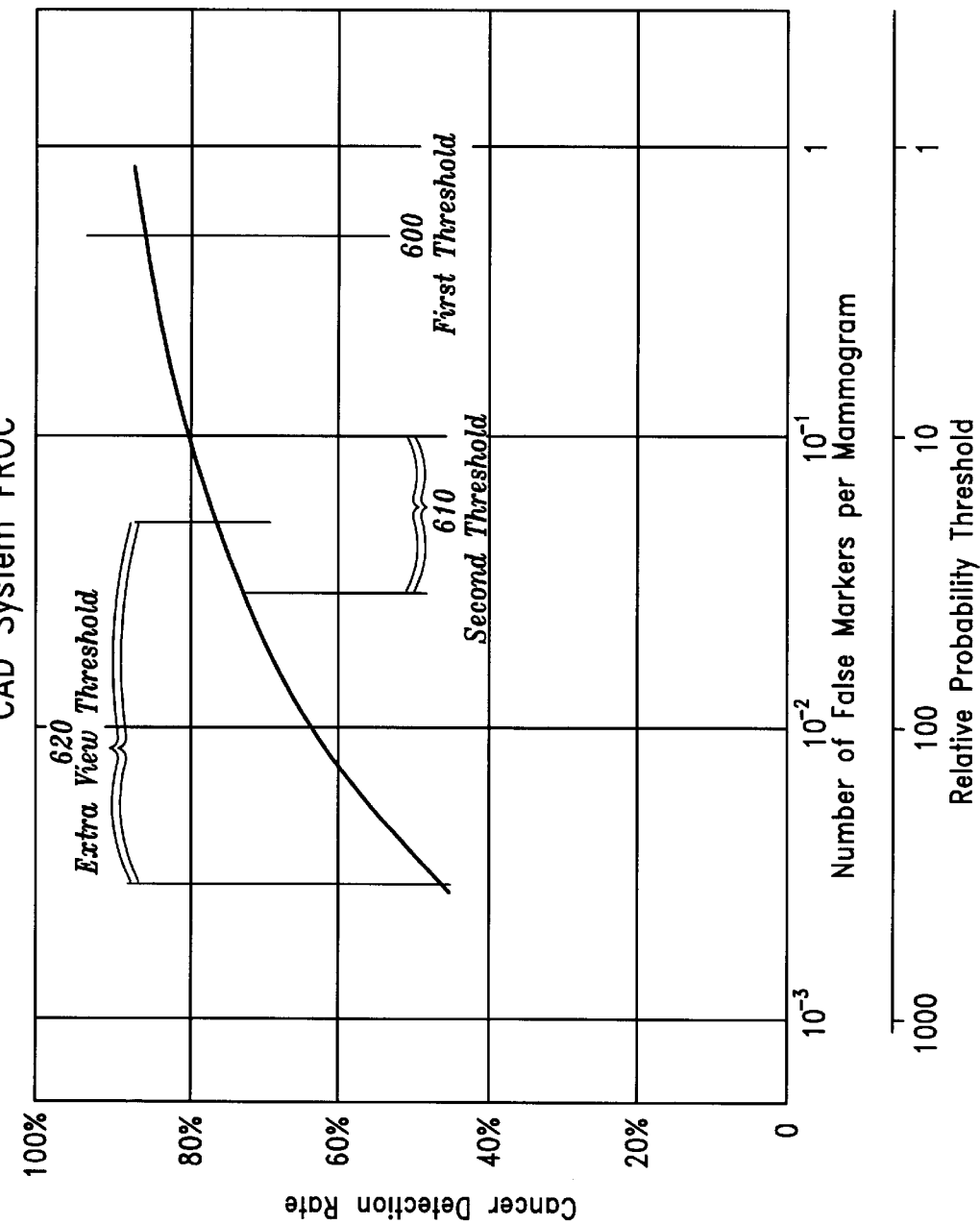
FIG. 3 is a FROC curve of a CAD system illustrating, according to a third embodiment, the selection and placement of two different probability thresholds for two markers.

FIG. 3 is a FROC (free response ROC or receiver operating characteristics) curve of a CAD system, where the system's cancer detection rate is plotted against the locational marker's relative probability threshold setting. That is, the CAD system's detection rate varies inversely with the logarithm of the probability threshold setting. As the probability threshold is lowered, the detection rate increases. The false marker rate on non-cancer mammograms is inversely proportional to the probability threshold setting. That is, as the probability threshold is lowered, the false marker rate increases. Therefore, the FROC curve of a CAD system, plotting the system's cancer detection rate against the system's false marker rate on non-cancer mammograms, is a measure of the system's performance. Referring to FIG. 3, according to a third embodiment, a user of the method and system described herein can select the probability thresholds with the guide of the FROC curve. For example, a first probability threshold setting point 600 is selected to display many subtle abnormalities with a high cancer detection rate of 85% and a rather high false marker rate of 0.5 per normal mammogram. This false marker rate is equivalent to approximately 500 false marks per cancer detected. A typical physician's recall rate for diagnostic examination can be 5 to 20 per cancer detected. Thus, this false marker rate is substantially higher than the rate of abnormalities that a physician would typically consider to be significant. Not knowing the probability or significance of each marker and not wishing to overlook significant cancers, a physician may elect to regard all markers as equally significant and thus spend equal amount of time to dismiss each marker. Thus, the physician may spend too much time on the task of dismissing low probability markers. On the other hand, not wishing to miss subtle cancers, the CAD system designer may not want to offer a system with too high a probability threshold setting. A solution to this problem is provided in the above described exemplary embodiments. Knowing the probability of the markers, the physician could then efficiently allot his or her time in assessing/dismissing the markers. With color, size or numerical probability indicators, some physicians may feel the display is too busy or too complex for efficient readings of the mammograms. A solution in such a case is to select a second threshold, for example at 610, set in the range of approximately 1 to 5 times a typical physician's recall rate for diagnostic examination, to thereby separate out high probability markers that appear only occasionally (for example marker 56, which appears at a rate of approximately once every 50 mammograms and marker 57, which appears once every 10 mammograms), so that the physician can better allot his or her time in assessing/dismissing the markers. Depending on the physician's recall rate, the threshold 610 should be set at a rate of, e.g., once every 4 to 250 mammograms. In the more developed countries, where the breast cancer rates tend to be higher than in less developed countries, the second threshold 610 at a setting of one marker every 10 to 40 mammograms is a reasonable compromise. A separate marker, differing from the first threshold markers in color, shape or size, can be used for the second threshold. Of course, some physicians may prefer more than two thresholds, in which case the system can accommodate that choice as well.

FIG. 3 also illustrates, according to a fourth embodiment, the selection and placement of an "extra view markers" threshold 620. This threshold can be set at or near the physician's typical recall rate for diagnostic examination. That is, depending on the physician's recall rate, an "extra view marker" is displayed to the technician to suggest extra views at a rate of once every 20 to 250 mammograms.

Referring to FIG. 1, according to a fifth embodiment, a control device 95 is provided to the user to allow the user to select and vary the probability threshold for the display of locational markers. By varying the probability threshold, the user can selectively set the probability threshold to taste or selectively view the markers with very low probability to markers with very high probability.

What is claimed is:

1. A method comprising:
    processing a mammogram in digital form to detect suspected abnormalities;
    creating an annotated map of suspected abnormalities detected in said processing;
    wherein said map shows both locations of suspected abnormalities and values related to confidence levels that suspected abnormalities are true abnormalities;
    said confidence levels being user selectable; and
    displaying both the mammogram and the annotation map to a user.

2. A method as in claim 1 comprising supplying an x-ray film mammogram and digitizing the film mammogram to thereby generate the mammogram in digital form that is processed in said processing.

3. A method as in claim 1 in which said processing includes converting said digital mammogram from one digital format to another digital format.

4. A method as in claim 1 including selecting a first threshold of said confidence level and using a first notation to show suspected abnormalities in said map detected in accordance with the first threshold.

5. A method as in claim 4 including selecting an additional, second threshold of said confidence levels, different from the first threshold, and using a second notation, different from said first notation, to show suspected abnormalities detected in accordance with the second threshold.

6. A method as in claim 5 including selecting a third threshold, different from said first and second thresholds, and using a third notation, different from said first and second notations, to show suspected abnormalities detected in accordance with the third threshold.

7. A method as in claim 1 in which said map shows said values related to confidence levels as numerical values.

8. A method as in claim 1 in which said map shows said values related to confidence levels as different colors for different ranges of values.

9. A method as in claim 1 in which said map shows said values related to confidence levels as location markers that are differently sized in accordance with said values.

10. A method as in claim 1 in which said displaying comprises displaying a mammogram at a lightbox and displaying an annotated map corresponding thereto at a monitor below and adjacent the mammogram.

11. A method as in claim 10 in which said displaying comprises displaying a reduced size version of the mammogram superimposed and registered with said map at said monitor.

12. A method as in claim 1 in which said displaying comprises displaying said mammogram in digital form at a monitor and displaying said annotated map on the same monitor, at a location spaced from a display of a breast in said mammogram.

13. A method as in claim 1 including printing a film version of said mammogram in digital form and of said annotated map, wherein said displaying comprises displaying said film version at a lightbox, with said annotated map spaced from a display of a breast in said film mammogram.

14. A system comprising:
    a source of a mammogram in digital form;
    a processor processing said mammogram digitally to detect suspected abnormalities therein;
    said processor creating as a result of said processing an annotated map showing both locations of suspected abnormalities and values related to a likelihood that the abnormalities are true abnormalities;
    a display coupled with said processor to display both the image of a breast represented in said mammogram and said annotation map.

* * * * *